(12) United States Patent
Knight et al.

(10) Patent No.: US 6,587,213 B1
(45) Date of Patent: Jul. 1, 2003

(54) NONDESTRUCTION COATING ADHESION EVALUATION USING SURFACE ULTRASONIC WAVES AND WAVELET ANALYSIS

(75) Inventors: Bryon Knight, Averill Park, NY (US); Julius Frankel, Rensselaer, NY (US); Moayyed Hussain, Menands, NY (US); Jeffrey Braunstein, Basement Troy, NY (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 204 days.

(21) Appl. No.: 09/716,115

(22) Filed: Nov. 15, 2000

(51) Int. Cl.[7] ................................................. G01B 9/02
(52) U.S. Cl. ..................................... 356/502; 356/241.2
(58) Field of Search ............................. 356/502, 432 T, 356/486, 492, 241.1, 241.2, 626

(56) References Cited

U.S. PATENT DOCUMENTS

| | | | |
|---|---|---|---|
| 4,541,280 A | 9/1985 | Cielo et al. ................... 73/603 |
| 5,268,967 A | * 12/1993 | Jang et al. ................... 382/132 |
| 5,724,138 A | 3/1998 | Reich et al. ................. 356/359 |
| 6,181,431 B1 | * 1/2001 | Siu ............................. 356/432 |

* cited by examiner

Primary Examiner—Samuel A. Turner
Assistant Examiner—Michael A. Lyons
(74) Attorney, Agent, or Firm—John F. Moran

(57) ABSTRACT

The present invention is a nondestructive and quantitative laser ultrasonic laser apparatus and associated method for determining adhesion quality of a coating on a substrate. The apparatus of the invention is preferably a pulsed laser for generation and Michelson-type interferometer based system and includes a rotary probe head assembly for making evaluations within a cylindrical test specimen. The method of the invention includes data analysis that uses acquired data from the ultrasonic laser apparatus and computes the dispersion relation or curves (frequency versus velocity) using a ridge-following technique in wavelet analysis and from this, outputs the adhesive quality of the coating by comparing it with a theoretically based determination of a particular coating/substrate bond system. The invention is used for evaluating adhesion quality of coatings used in a gun bore.

11 Claims, 8 Drawing Sheets

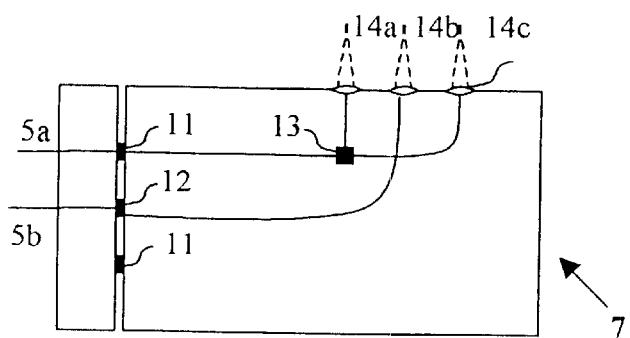 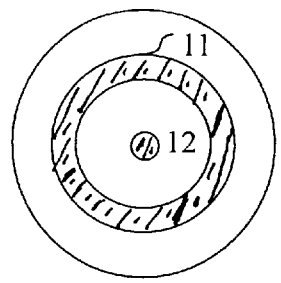
FIG. 2   FIG. 3
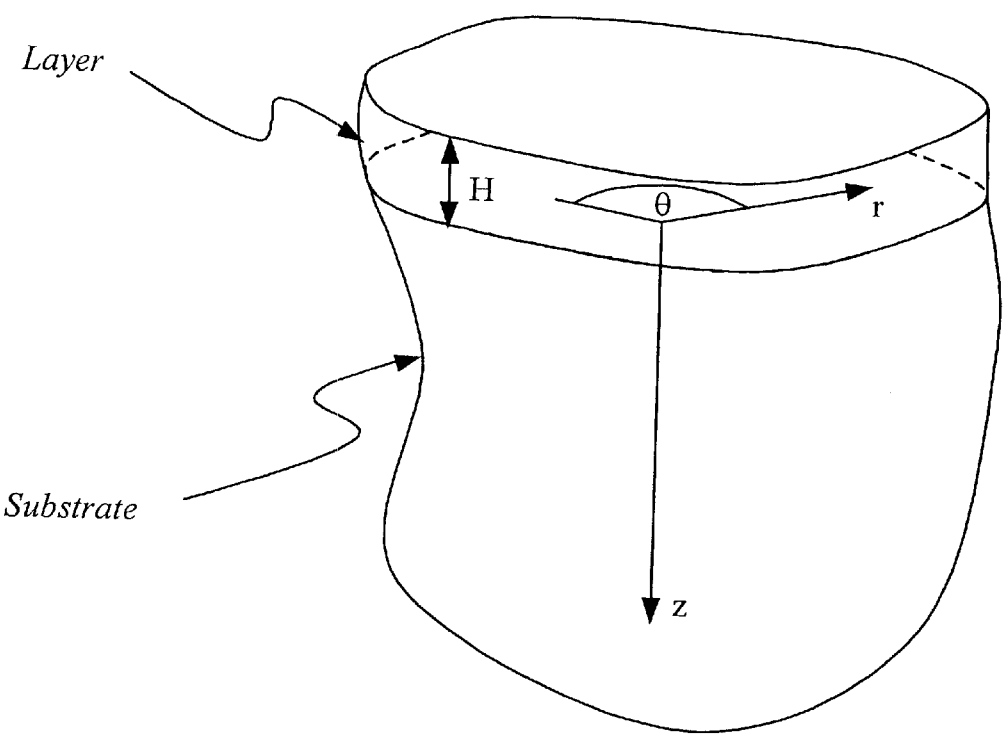
FIG. 4

NONDESTRUCTION COATING ADHESION EVALUATION USING SURFACE ULTRASONIC WAVES AND WAVELET ANALYSIS

STATEMENT OF GOVERNMENT INTEREST

The invention described herein may be manufactured and used by or for the United States Government for Governmental purposes without the payment of any royalties thereon.

BACKGROUND OF THE INVENTION

1. Field of the Invention

The present invention relates to a non-destructive method and apparatus for testing adhesive quality of a metallic coating on metallic substrates formed in either a flat or cylindrical specimen. In particular, the present invention relates to testing of metal coatings on the inside of a gun bore and evaluation of the adhesion quality of such coatings.

2. Description of the Prior Art

Coatings serve several functions; one is to extend the life of the component. After all precautions have been taken in manufacturing, failure of components is frequently initiated at the surface, and this is particularly true in an aggressive environment. Some coatings are deposited to protect the surface of the substrate. The coating protects against corrosion, fatigue, temperature, and erosive effects. Any coating can either fail by loss of adhesion.

The problem of evaluating metallic coatings has always existed. Chromium coatings on gun tubes have been used for fifty years. At present there is no quantitative means for the evaluation of metallic coatings. The scratch test uses a smoothly rounded stylus to scratch the surface of the film as the load is gradually increased. The load at which the film under the stylus is detached and a clean scratch is created, has been used in the past to indicate the "quality" of the coating. It is a comparative-type test. This test is destructive and hence not applicable to a part in use. Presently, there does not exist a non-destructive way of evaluating a coating, and especially of evaluating a coating which is not readily accessible. For example chromium has been plated on the bore of gun tubes for over fifty years, and the way of evaluating the coating has been to actually fire the gun and visually observe the amount of coating not adhering to the bore. Previously, the coating had to be destroyed for it to be evaluated. This evaluation has included visual, qualitative, and comparative analysis.

Ultrasonic inspection is one of the most important non-destructive techniques for inspecting materials and structures. Conventional ultrasonic inspection suffers from two important limitations: first, there is need of contact between the transducer and the inspected part and most often need of coupling fluid bath or fluid column (such as water) to transmit ultrasound and secondly the transducer should be properly oriented with respect to the surface when single side inspection is performed (operation in reflection or pulse echo mode). Thus, inspection of samples at elevated temperature or complex geometry is difficult. Such techniques cannot readily be used in a preferred use of the invention for examining layered metal coatings within a gun bore.

Such limitations are circumvented by laser ultrasonics, an ultrasonic inspection technique, which uses lasers to generate and detect ultrasound. For generation, a high power short pulse laser is generally used and the ultrasonic waves are produced by the surface stresses induced by the heat generated by laser absorption or by the recoil effect following surface ablation. For detection, a continuous wave or long pulse laser is used in association with a Michelson interferometer which is sensitive to the ultrasonic surface motion and gives a signal representative of this motion.

U.S. Pat. No. 5,724,138 teaches a laser ultrasonics technique that characterizes a composite dispersive response signal from a semiconductor wafer under analysis for temperature detection during processing of the wafer. An entire dispersive response signal is analyzed by using discrete wavelet transform analysis. However, this technique does not teach or suggest apparatus or method, which determines quantitatively adhesion quality of a metal coating on a substrate, or mechanisms for doing such evaluations where the examined structure has a cylindrical surface such as a gun barrel. Thus, there is need for an integrated approach for examining metal-coated surfaces as to their adhesive qualities using laser ultrasonic apparatus.

SUMMARY AND ADVANTAGES OF THE INVENTION

The present invention is a nondestructive and quantitative laser ultrasonic apparatus and associated method for determining adhesion quality of a coating on a substrate. The apparatus of the invention is preferably a Michelson-type interferometer based system and includes a rotary probe head assembly for making evaluations within a cylindrical test specimen. The method of the invention can be used when the coating acoustic impedance is equal, greater or less than the substrate, and the coating layer is thin, i.e. situations where conventional ultrasonic techniques are not effective. The method of the invention includes data analysis that uses acquired data from the ultrasonic laser apparatus and computes the dispersion relation (frequency versus velocity) and from this, outputs the adhesive quality of the coating. In the analysis, a layer which has "good" adhesion to the substrate is attached by a "welded" bond and a layer which has "poor" adhesion attached by a "smooth" bond. In the analysis, the difference between these two cases is defined by the boundary conditions imposed on the coating layer and the substrate. The result of the analysis of the "welded" and "smooth" bonds of a test specimen shows a difference in the shapes of the respective dispersion curves. In wavelet analysis, differentiation between "good" and "poor" adhesion bonds is qualified and quantified using a ridge-following technique.

Accordingly, advantages of the invention using a laser ultrasonic apparatus and method include:

a) A system that enables rapid measurements at remote locations which are accessible to optical fibers, or direct laser beam incidence;

b) A system that can be used in industrial environments and does not require physical contact with the test specimen, which can have flat or cylindrical surfaces directly accessible to these laser beams; and c) A system and method that lends itself to automation such that the test specimen can be scanned efficiently by ultrasonic laser hardware and analyzed efficiently using a ridge-following technique in wavelet analysis by comparing theoretical results with analyzed experimental results of the test specimen.

Still further advantages will become apparent from consideration of the ensuing detailed description.

BRIEF DESCRIPTION OF THE DRAWING

FIG. 2 shows a cross-section of a probe head assembly for inspection of the inner bore of a cylindrical specimen.

FIG. 3 shows a transverse view of the optical coupler on the probe head assembly shown in FIG. 2, which allows the probe head to rotate while inside the cylindrical specimen.

FIG. 4 shows the layer and substrate and the coordinate system used by the invention.

In the drawings and constituted as such, like numerals indicate like parts.

DETAILED DESCRIPTION OF THE PREFERRED EMBODIMENT

The physical phenomenon associated with the present invention is that surface acoustic waves generated in a two-layer medium, travel in both the coating and the substrate. A characteristic of these waves is that the effective depth (distance from the surface) to which they travel is approximately equal to their wavelength. Thus the shorter wavelengths (higher frequencies) travel in the coating and the longer wavelengths (lower frequencies) travel mostly in the substrate. Therefore surface acoustic waves of intermediate wavelength are characteristic of both the layer and the half space and thus give information about the bond.

One ultrasonic laser apparatus, which can be used to obtain data using the method of the present invention for flat surfaces, is described in U.S. Pat. No. 4,541,280, by Paolo Cielo and Jean Bussiere (which is hereby incorporated by reference). This patent discloses the use of a laser signal generation and detection scheme of surface acoustic waves from the test specimen. When the laser pulse impinges on a surface of the test specimen, the temperature of the contact area rises and diffuses, causing a rapid expansion and contraction of the surface. This leads to the generation of a surface wave. The spatial width of the laser pulse and its time duration control the frequencies present in the pulse. In applications where flat surfaces are measured, the signal to noise ratio is enhanced due to convergence of circular wave in the center. Point detection is done at the center of the annulus.

Two extreme cases exist for adhesion of a layer to a half space as defined by Achenbach and Epstein, "Dynamic Interaction of a Layer and Half-Space", Journal of Engineering Mechanics Division; Proceedings of the American Society of Civil Engineers, October 1967, pp 27–42. A layer that has "good" adhesion to the half space is also known to constitute a "welded" bond and a layer that has "poor" adhesion is known to constitute a "smooth" bond. In the analysis, the difference between these two cases is defined by the boundary conditions imposed at the interface between the layer and the substrate. The result of the analysis of the "welded" and "smooth" bonds shows a difference in the shapes of the respective dispersion curves. Thus, differentiation between "good" and "poor" adhesion bonds is qualified and quantified using the ridge-following technique in wavelet analysis.

Examples of the "welded" bonds are analyzed, as discussed below, where chromium is electrodeposited on steel and tantalum is sputtered on steel. Also, examples of the "smooth" bonds are analyzed using tantalum that is epoxied on steel and nickel that is epoxied on copper. As shown below using experimental results that are compared to theoretical findings, that poor electroplated or sputtered coatings show differences from the "welded" dispersion curve, or similarities to the "smooth" dispersion curve.

Figure 1:
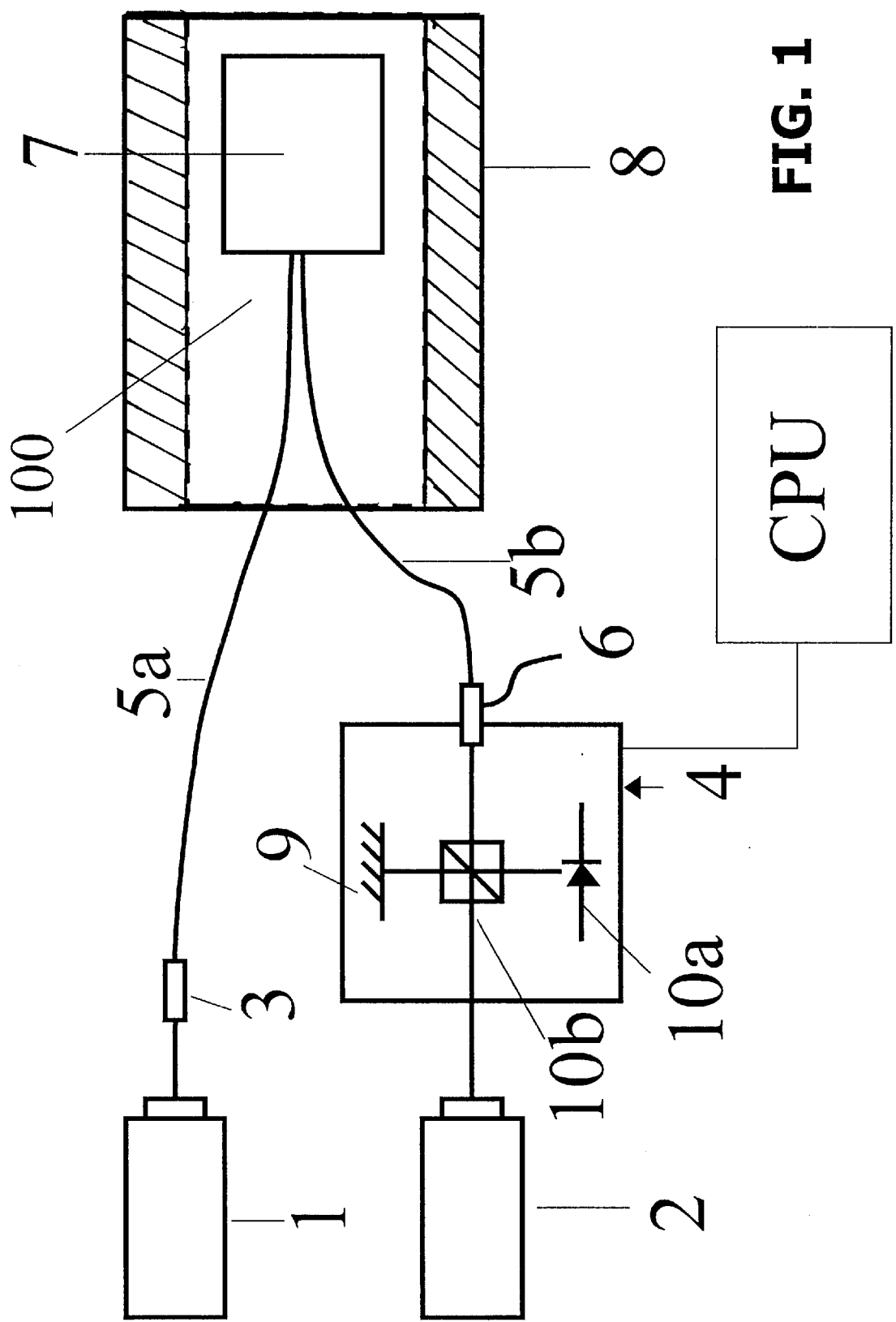
FIG. 1 shows an schematic for obtaining surface wave data of a coated inner bore of a cylindrical specimen.

Referring now to FIG. 1, one form of the laser ultrasonic apparatus is shown that is adapted for use inside a cylindrical test specimen 8 with inner surface 100. The apparatus includes at least two lasers, one being a high power laser 1 (preferably a pulsed laser source) for generation of surface waves on the test specimen and a detection laser 2 (for example a Helium-Neon Laser) which is the monochromatic light source for a Michelson-type interferometer 4. Optical fibers 5a and 5b are coupled to the lasers 1 and 2 respectively through optical couplers 3 and 6, and transmit the laser beams to a probe head assembly 7.

The Michelson-type interferometer 4 shown in FIG. 1, measures instantaneous displacement of a surface of the test specimen based upon the interference between the superposition of two monochromatic beams of light. The two coherent beams, which make up the interferometer, are the signal leg (moving) and the reference leg (static). The reference leg is a beam that travels to a fixed mirror 9 and back, and the signal leg is a beam that reflects off the surface of the test specimen. A monochromatic light source, such as a laser, is a practical source for this apparatus. The light source is divided into the reference and signal legs by a beam splitter 10b. The beam splitter also recombines the two beams; the resultant beam is detected by a photodetector 10a. The phase difference between the signal and reference legs determines the intensity of the resultant beam detected at the photodetector 10a. The theory of a Michelson interferometer is well known. This allows for the obtaining of very small displacements. Any other type of interferometer or other contact acoustic device can be used also as long as wave parameters can be measured which can be related to the frequency content of the wave.

Referring now to FIGS. 2 and 3, the probe head assembly 7 is shown in detail. The optical fibers 5a and 5b of FIG. 1 for the generation and detection lasers come into the probe head assembly at a back end of the assembly as shown. The probe head assembly rotates about a centerline of the probe head 15 through coupler 12 as shown, thereby enabling scanning of the cylindrical test specimen in a complete circular arc. Optical rotary couplers 11 and 12 transmit the generation laser beams and detection beams to the probe head 15 that rotates. Generation of surface acoustic waves in the test specimen is accomplished at two points through focusing lenses 14a and 14b equidistant from the detection lenses 14c keeping the two generation lens 14a and 14b and the detection lens 14c along a straight line. This increases the signal-to-noise ratio. The single optical fiber 5a that transmits the generation laser beam is split into separate fibers by optical coupler 13.

FIG. 3 shows a transverse view of the optical rotary couplers 11 and 12. The generation laser 3 is coupled to the lenses 14a and 14b, and the detection laser 6 is coupled through the interferometer 4 to the lens 14c. Both couplers 11 and 12 are centered about the rotational axis of the probe head assembly 7. The coupler for the laser 6 is bi-directional so that the signal can return to the interferometer 4.

The process of obtaining useful data begins with determination of the shape and location of the surface to be tested. If the surface is flat and readily accessible to direct laser beams from a pulsed laser and interferometer laser sources, the annular generation system as taught in U.S. Pat. No. 4,541,280 can be used. If the surface is not accessible to direct beams from a source, as in the case of a gun bore, optical fibers 5a and 5b are used to transmit both the impulse laser pulse to the surface and the detection laser beam to and from the same test specimen surface using the probe assembly 7. Thus, an appropriate generation laser beam is transported to the surface to excite the surface acoustic waves and the detection laser beam is transported to, and reflected off the surface. The resultant signal from the interferometer can then be detected using a photodetector 10a. The output of the detector 10a is provided to the central processing unit (CPU) wherein a ridge-following technique of wavelet analysis signal processing is used in the manner described below.

Analysis Using Ridge-Following Technique in Wavelet Analysis

The frequency dependence of the acoustic wave velocity is a means of determining the coating quality. Such a theoretical problem is solved by Achenbach and Epstein, as discussed above. This is done for straight crested surface waves. There, the boundary conditions between the layer (coating) and the substrate are used to define the nature of adhesion of the coating to the substrate. These boundary conditions are defined in terms of stresses and displacements at the free layer interface and the layer-half space interface. The application of the stress and displacement boundary conditions at the interface results in a six by six matrix, which contains the elastic properties, velocities and frequencies. The solution which involve these properties, is obtained by zeroes of the determinant of this matrix.

The method of the invention provides a solution for the case where surface waves are generated in a layer on a half space as shown in FIG. 4, for axisymmetric generation and detection in the center. Using boundary conditions analogous to Achenbach and Epstein as discussed above, the dispersion relations for the both cases are obtained for "welded" and "smooth" contact surfaces. They are described by the following boundary conditions. For "welded" contact, the boundary conditions are:

$$\sigma_{z_a}=0, \tau_{rz_a}=0, \tau_{\theta z_a}=0 \text{ at } z=-H \tag{1}$$

$$u_{z_a}=u_{z_b}, u_{r_a}=u_{r_b}, u_{\theta_a}=u_{\theta_b}, \tau_{rz_a}=\tau_{rz_b}, \tau_{\theta z_a}=\tau_{\theta z_b}, \sigma_{z_a}=\sigma_{z_b} \text{ at } z=0 \tag{2}$$

and the "smooth" contact boundary conditions are:

$$\sigma_{z_a}=0, \tau_{rz_a}=0, \tau_{\theta z_a}=0 \text{ at } z=-H \tag{3}$$

$$u_{z_a}=u_{z_b}, \tau_{rz_a}=0, \tau_{rz_b}=0, \tau_{\theta z_a}=0, \tau_{\theta z_b}=0, \sigma_{z_a=\sigma z_b} \text{ at } z=0. \tag{4}$$

The solutions of equation of motion and stress strain relations with these boundary conditions lead to two sets of nine homogenous equations involving geometric parameters, elastic constants, frequency and acoustic velocity. For the solution to exist, these two 9×9 determinants have to vanish for a set of velocities in a frequency range leading to the dispersion relation for the given geometry and material properties. Further, in absence of torsional motion, these determinants reduces to a 6×6 matrice as shown by equations (5) and (6) below. The solution using the welded contact boundary conditions for a straight crested wave is:

$$\begin{vmatrix} \frac{1+s_a^2}{2}e^{-q_akH} & -s_a e^{-s_akH} & \frac{1+s_a^2}{2}e^{q_akH} & s_a e^{s_akH} & 0 & 0 \\ 2q_a e^{-q_akH} & -(1+s_a^2)e^{-s_akH} & -2q_a e^{q_akH} & -(1+s_a^2)e^{s_akH} & 0 & 0 \\ -1 & s_a & -1 & -s_a & 1 & -s_b \\ -q_a & 1 & q_a & 1 & q_b & -1 \\ \frac{1+s_a^2}{2\sigma_a} & \frac{-s_a}{\sigma_a} & \frac{1+s_a^2}{2\sigma_a} & \frac{s_a}{\sigma_a} & -\frac{(1+s_b^2)\mu_b}{2\sigma_a\mu_a} & \frac{s_b\mu_b}{\sigma_a\mu_a} \\ 2q_a & -(1+s_a^2) & -2q_a & -(1+s_a^2) & \frac{-2q_b\mu_b}{\mu_a} & \frac{(1+s_b^2)\mu_b}{\mu_b} \end{vmatrix} \tag{5}$$

The solution using the "smooth" contact boundary conditions is:

$$\begin{vmatrix} \frac{1+s_a^2}{2}e^{-q_akH} & -s_a e^{-s_akH} & \frac{1+s_a^2}{2}e^{q_akH} & s_a e^{s_akH} & 0 & 0 \\ 2q_a e^{-q_akH} & -(1+s_a^2)e^{-s_akH} & -2q_a e^{q_akH} & -(1+s_a^2)e^{s_akH} & 0 & 0 \\ -q_a & 1 & q_a & 1 & q_b & -1 \\ \frac{1+s_a^2}{2\sigma_a} & \frac{-s_a}{\sigma_a} & \frac{1+s_a^2}{2\sigma_a} & \frac{s_a}{\sigma_a} & -\frac{(1+s_b^2)\mu_b}{2\sigma_a\mu_a} & \frac{s_b\mu_b}{\sigma_a\mu_a} \\ 2q_a & -(1+s_a^2) & -2q_a & -(1+s_a^2) & 0 & 0 \\ 0 & 0 & 0 & 0 & -\frac{2q_b\mu_b}{2\mu_a} & \frac{(1+s_b^2)\mu_b}{\mu_b} \end{vmatrix} \tag{6}$$

The converging ultrasonic surface wave signal generated by an impulse laser impinging on the surface in an annulus can be approximated as a sum of a set of Gaussian signals each having its own center frequency and its own envelope and each corresponding to a band limited signal. The signal can be represented as:

$$f(t) = \sum_n a_n e^{-\left(\frac{t-t_n}{\beta_n}\right)^2} e^{j\omega_n(t-t_n)} = \sum_n f_n(t) \quad (7)$$

where n is number of Gussian packets with amplitude $a_n$, decay parameter $\beta_n$, center frequency $\omega_n$ and $t_n$ is the time delay given by:

$$t_n = \frac{d}{v_n} \quad (8)$$

where d is the radius of the circular annulus and $v_n$ is the velocity of the packet. For each packet d remains the same, thus a shorter $t_n$ corresponds to higher velocity of the wave packet.

As previously noted, Rayleigh surface waves become dispersive in the presence of a protective coating layer. Such dispersion, giving the relation, between frequency $\omega_n$ and group velocity $v_n$ depends on the material properties of coating and substrate as well as the quality of the bond. Estimation of the dispersion curve is central in characterization the quality of the bond. Since each packet is nearly Gaussian, the wavelet transform with frequency modulated Gabor mother wavelet, which is also Gaussian, leads to an optimum correlation determination.

In this section, analytical illustration is made of the peaks of the wavelet transform of each packet corresponds to a point on the dispersion curve.

The wavelet transform of f(t) is given by (A Wavelet Tour of Signal Processing, S. Mallat. Academic Press, (1998):

$$Wf(u, s) = \int_{-\infty}^{\infty} f(t) \frac{1}{\sqrt{s}} \psi^*\left(\frac{t-u}{s}\right) dt \quad (9)$$

with s frequency scaling and u time delay.
Consider the modulated wavelet with Gabor window:

$$\psi(t) = e^{j\eta t} g(t) \quad (10)$$

$$g(t) = \frac{1}{(\pi\sigma^2)^{\frac{1}{4}}} e^{-\frac{t^2}{2\sigma^2}} \quad (11)$$

with center frequency $\eta$ and variance of $\sigma^2$. Now consider a single packet of the signal:

$$f_n = a_n e^{-\left(\frac{(t-t_n)}{\beta_a}\right)^2} e^{j\omega_n(t-t_n)}, \quad (12)$$

$$Wf_n(U, S) = \langle f_n, \psi_{u,s} \rangle = \int_{-\infty}^{\infty} f_n(t) \frac{1}{\sqrt{s}} \psi^*\left(\frac{t-u}{s}\right) dt \quad (13)$$

$$= a_n (4\sigma^2\pi)^{\frac{1}{4}} \beta_n \frac{\sqrt{s}}{\gamma_n} e^{j\omega_n(u-t_n)}$$

$$e^{j\frac{2s\sigma^2}{\gamma_n}(\eta-\omega_n s)(u-t_n)} e^{-\left(\frac{u-t_n}{\gamma_n}\right)^2}$$

$$e^{-\left(\frac{\sigma\beta_n(\eta-\omega_n s)}{\sqrt{2}\,\gamma_n}\right)^2}$$

with $\gamma_n^2 = \beta_n^2 + 2s^2\sigma^2$, the energy from equation (13) is given by:

$$|Wf_n(U, S)| = a_n(4\sigma^2\pi)^{\frac{1}{4}} \beta_n \frac{\sqrt{s}}{\gamma_n} e^{-\left(\frac{u-t_n}{\gamma_n}\right)^2} e^{-\left(\frac{\sigma\beta_n(\eta-\omega_n s)}{\sqrt{2}\,\gamma_n}\right)^2} \quad (14)$$

The above expression consists of two decaying exponetials, one in the time domain and the other in frequency domain. For a simple packet it reaches maximum value at a single point given by:

$$u_n = t_n = \frac{d}{v_n} \quad (15)$$

$$\xi_n = \left(\frac{\eta}{s}\right)_n = \omega_n \quad (16)$$

Equation (15) with equation (8) gives a single point in the frequency-velocity plane of the wavelet transform of a single packet. The wavelet transform of the complete signal is given by:

$$Wf(u, s) = \sum_n Wf_n(u, s) \quad (17)$$

and hence the ridges of the above transform give the dispersion curve. For numerical purposes we use the Fourier transform property of the convolution:

$$Wf(u,s) = \langle f(t), \psi_{u,s} \rangle = f * \bar{\psi}_s(u) \quad (18)$$

with:

$$\bar{\psi}_s(t) = \frac{1}{\sqrt{s}} \psi^*\left(-\frac{t}{s}\right) \quad (19)$$

and the Fourier transform is given by:

$$\hat{\bar{\psi}}(\omega) = \sqrt{s}\ \psi^*(s\omega) = (4\pi s^2 \sigma^2)^{\frac{1}{4}} e^{-\frac{\sigma^2}{2}(s\omega-\eta)^2} \quad (20)$$

Thus it is not necessary to decompose the original signal into packets. Use of fast Fourier Transforms (FFT) avoid numerical integration altogether, and provides relatively fast computation using mathematical computer software such as MATLAB (registered trademark). Once the FFT transform calculations are accomplished, the dispersion curve becomes the locus of the ridges of the transform in a frequency-velocity plane, see Analysis of Dispersive Ultrasonic Signal by the Ridges of the Analytic Wavelet Transform. A. Abbate et al. QNDE 18A pp. 703–710. (1999).

Method of Using the Invention

A. Data Acquisition

1. For a flat surface as a test specimen, which is readily accessible to laser beams, well known systems such as that taught in U.S. Pat. No. 4,541,280 using a laser system as discussed above can be used. This provides an annular generation and detection using a pulsed laser source of the flat surface.

2. If the surface of the test specimen is non-accessible to direct laser beams and not flat, then the system discussed above and shown in FIGS. 1, 2 and 3 is used wherein optical fibers are used for the annular generation and detection of pulsed laser source of the annular surface.

a. The pulsed laser beam of appropriate temporal and spatial width is projected onto the surface of the test specimen and a surface wave is generated.

b. The continuous wave (CW) that is reflected from the probed test specimen surface is combined with a CW from the reference laser source 6 and the combined signal strikes the photodetector 10a surface.

c. The resultant intensity of the combined signals generates a voltage, which is observed data from the interferometer 4.

d. The data is conditioned, filtered, averaged and stored by appropriate central processing unit (CPU) coupled to the photodetector 10a. The resultant data represents the time dependence of the normal displacement of the surface wave at the focal point of the detection laser 6.

B. Data Analysis

1. The ridge-following technique in wavelet analysis is applied to data obtained and the dispersion curve is generated by a computer. This curve is compared with the dispersion curve resulting from the theoretical dynamic analysis of surface waves in a layer and substrate. With input to the matrix equations (5) and (6) of the elastic constants of the layer and substrate the dispersion curves for the "smooth" and "welded" bond can be obtained for comparison.

2. The experimental and theoretical dispersion curves are compared, and the type of bonding is obtained.

EXAMPLES

Referring now to FIGS. 5a–d, dispersion curves resulting from the transcendental relationship, using matrices defined in equations (5) and (6) above, between Rayleigh velocity and the frequency for the smooth and welded boundary conditions are shown. Two cases are considered for each set of boundary conditions; first case is where the Rayleigh velocity of the coating is lower than the Rayleigh velocity of the substrate (coating acoustically less stiff than substrate), and the second case is where the Rayleigh velocity of the coating is higher than the Rayleigh velocity of the substrate (coating acoustically more stiff than substrate). The cases shown in FIGS. 5a–d are provided as follows:

TABLE 1

|  | Coating acoustically less stiff than substrate | Coating acoustically more stiff than substrate |
| --- | --- | --- |
| Welded Contact |  |  |
| Sample Method Coating Thickness | Tantalum on Steel Sputtered 0.0035 inches | Chromium on Steel Electrodeposited 0.0036 inches |
| Smooth Contact |  |  |
| Sample Method Coating Thickness | Tantalum on Steel Epoxied 0.005 inches | Nickel on Copper Epoxied 0.005 inches |

Figure 5A:
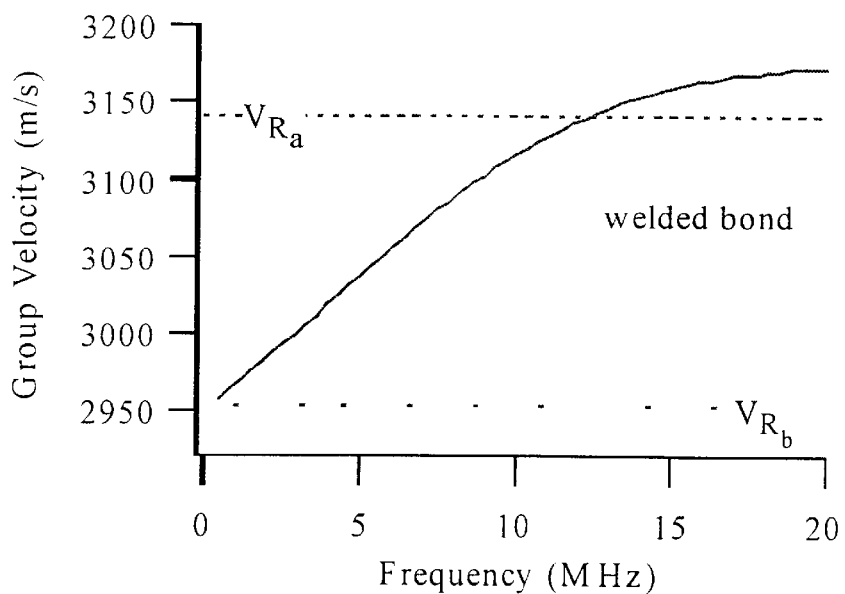
FIGS. 5a, 5b, 5c and 5d show theoretical dispersion curves calculated from the experimental parameters studied of examples discussed in Table 1 of specimens that are acoustically more stiff and less stiff than the substrate in specimens having both "welded" and "smooth" contact bonds.
Figure 5B:
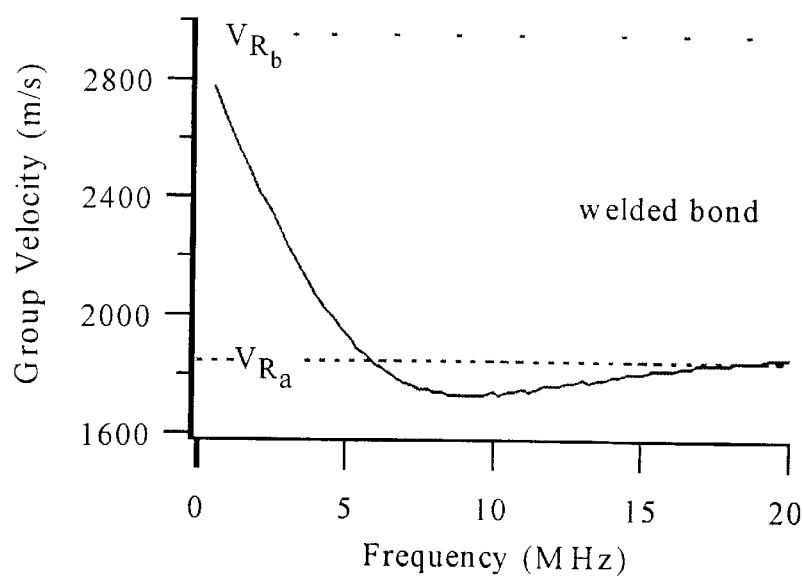
Figure 5:
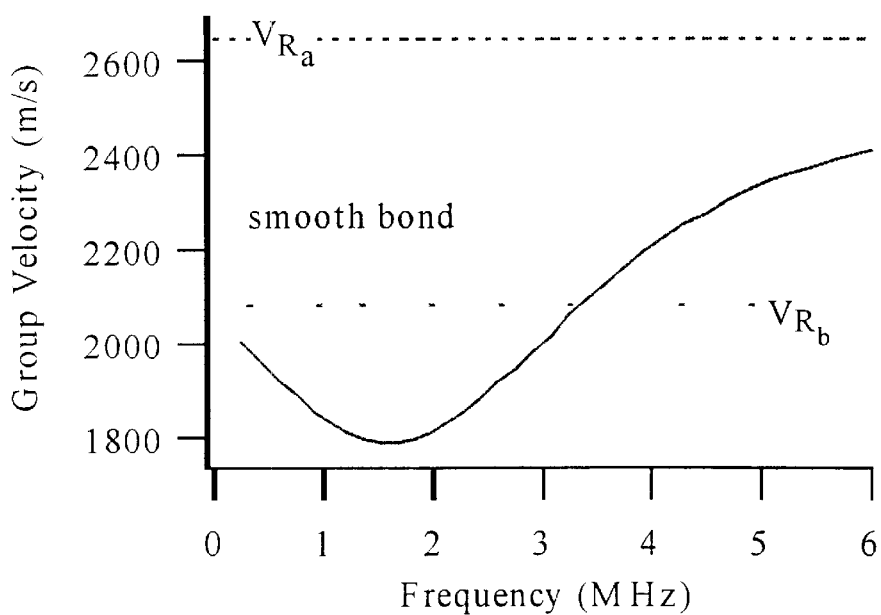
Figure 5D:
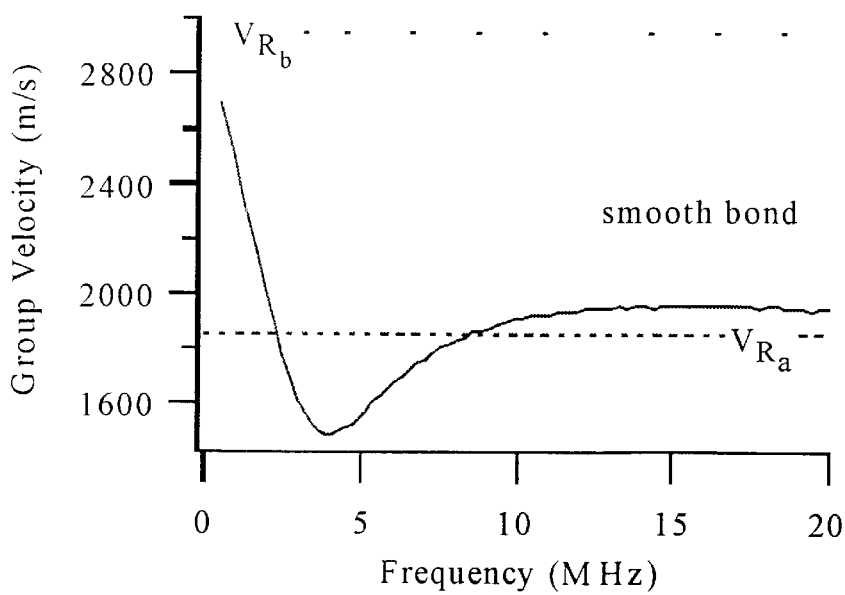
Figure 6A:
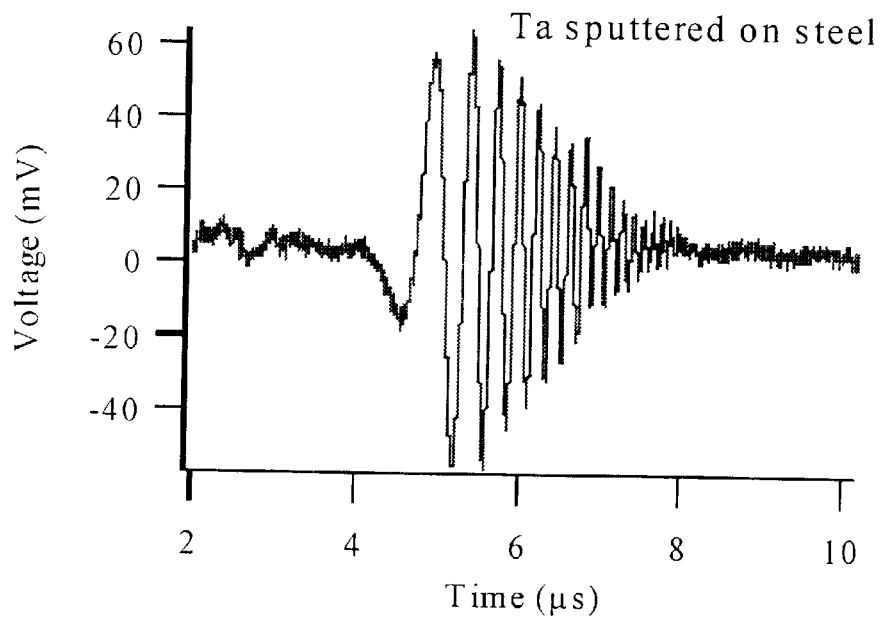
FIGS. 6a, 6b, 6c and 6d show both experimental waveforms from laser generated surface waves on "welded" contact test specimens as discussed in Table 1 with their corresponding dispersion curves obtained with analysis using the invention.
Figure 6B:
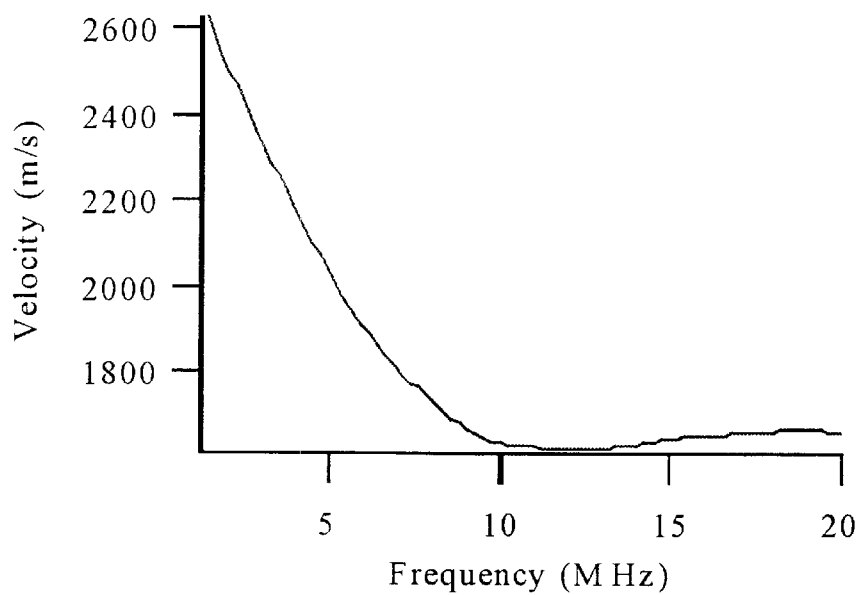
Figure 6:
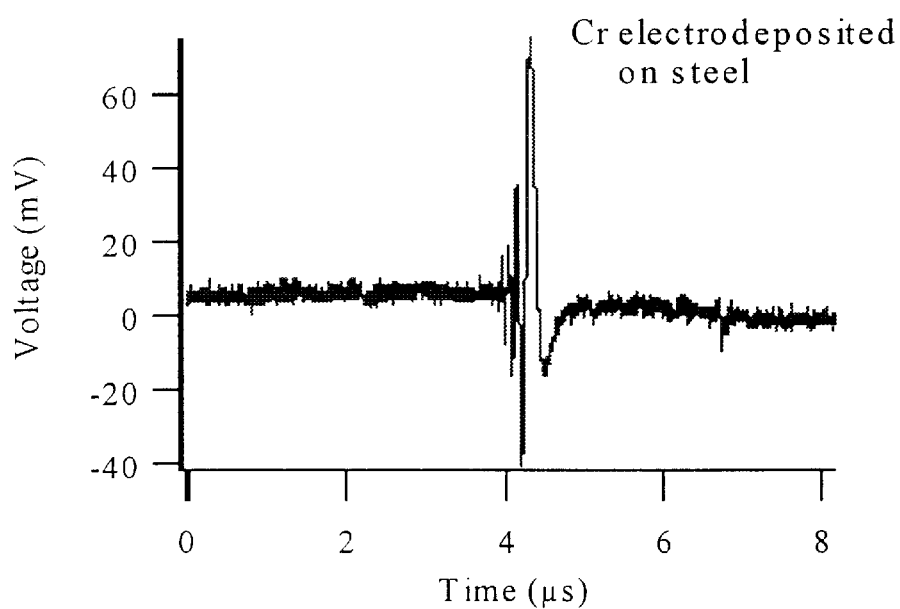
Figure 6:
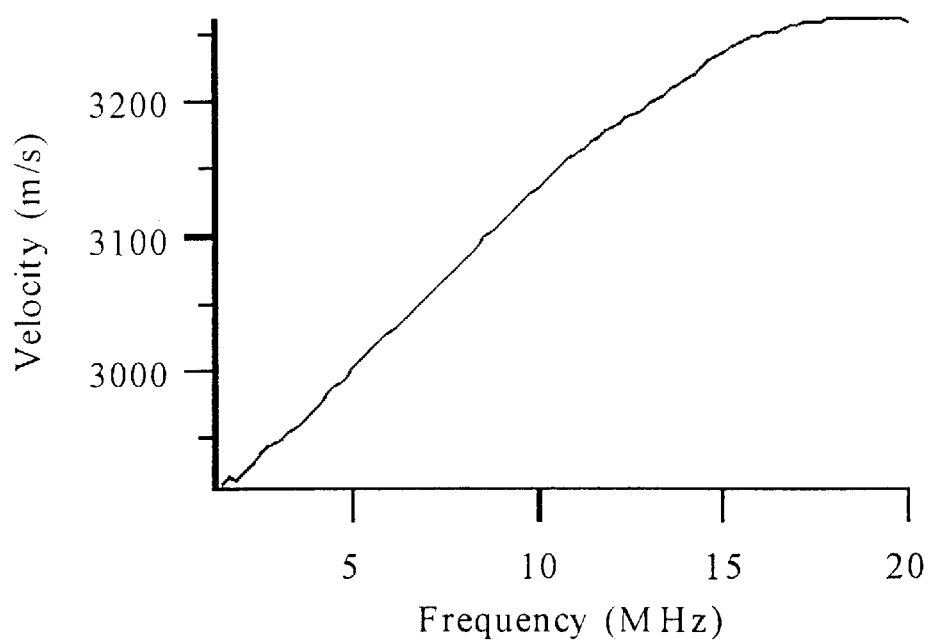
Figure 7A:
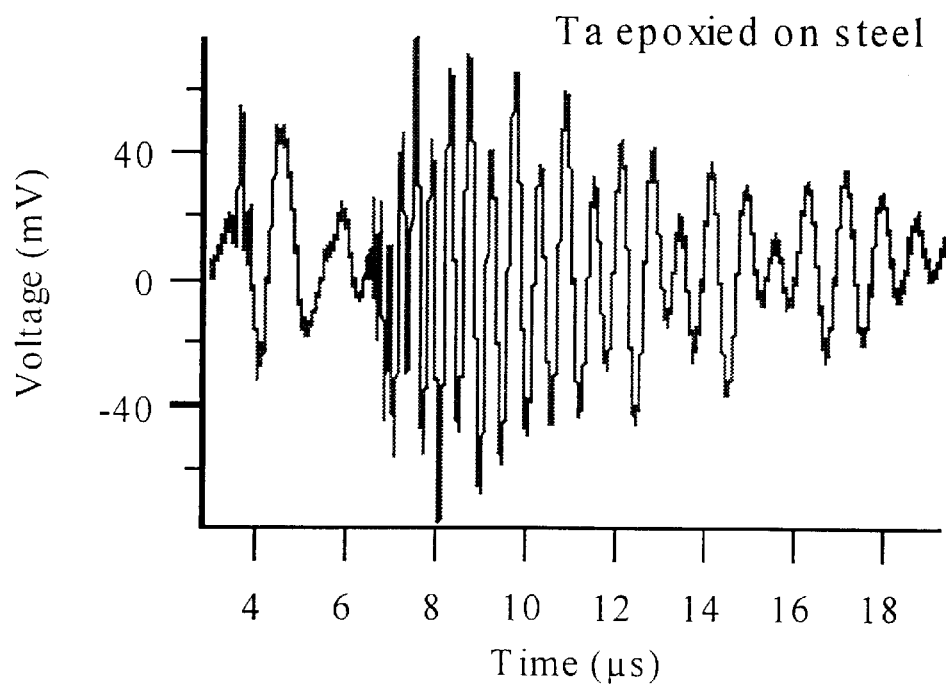
FIGS. 7a, 7b, 7c and 7d show both experimental waveforms from laser generated surface waves on "smooth" contact test specimens as discussed in Table 1 with their corresponding dispersion curves respectively.
Figure 7B:
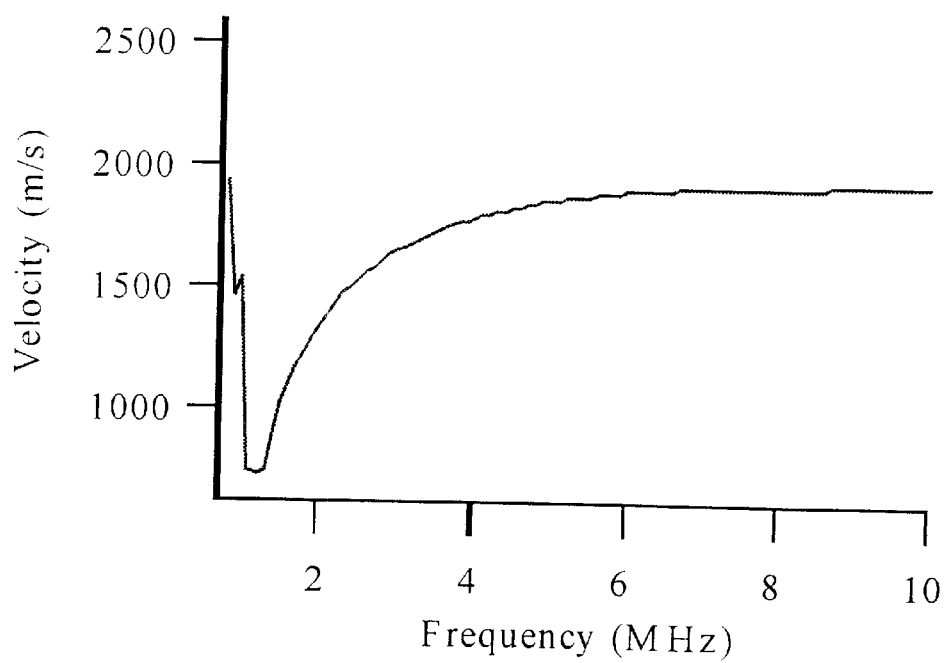
Figure 7:
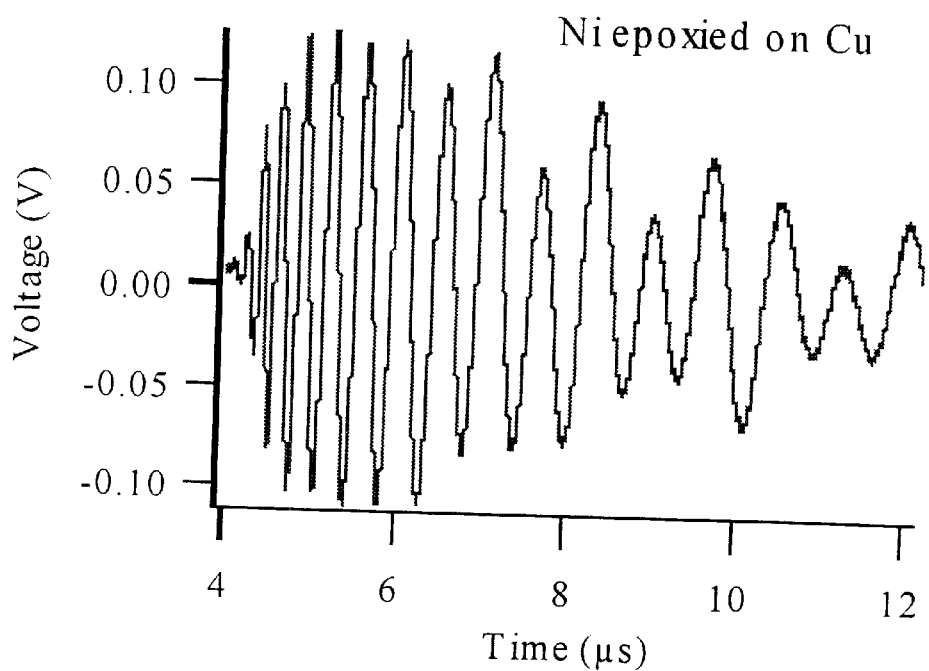
Figure 7D:
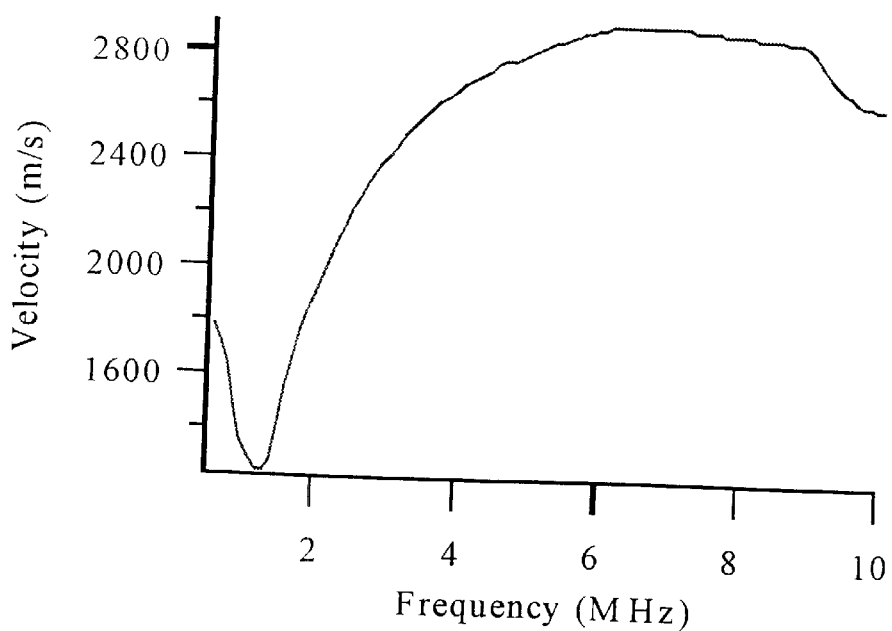

As shown in FIGS. 5a–d, theoretical dispersion curves are calculated from the experimental parameters, wherein FIG. 5a shows a "weld" contact coating that is acoustically more stiff than the underlying substrate. FIG. 5b shows a less stiff acoustic quality of a "weld" contact coating compared to the underlying substrate. FIG. 5c shows a "smooth" coating that is acoustically more stiff than the underlying substrate. FIG. 5d shows an acoustically less stiff "smooth" coating compared to the underlying substrate. VRa and VRb are Rayleigh velocities of the layer and substrate, respectively. The curves in FIGS. 5a–d are based on the elastic properties of the materials used for the experimental tests, as listed in Table 1.

Experimental data and resulting dispersion curves are shown in FIGS 6a–d and in view of Table 1, wherein examples of the "welded" contact bond, chromium is electrodeposited on steel and tantalum is sputtered on steel. The experimentally determined dispersion curves thus obtained using wavelets in both cases show close similarity to an expected shape from the theoretical analysis, with the high and low frequency values of the Rayleigh velocity corresponding to the coating and substrate, respectively, and a smooth transition between these two values at the intermediate frequencies.

Referring now to FIGS. 7a–d and in view of Table 1, the epoxied sheets of tantalum and nickel on steel and copper respectively, approximates the "smooth" boundary condition between a layer and a half space. The experimentally determined dispersion curves, have an approximate shape found from the theoretical analysis, but show a dip in the low frequency region. The low frequency end of the curves provides the substrate Rayleigh velocity, whereas the higher frequency end gives the velocity for the metal coating. Even the raw data from the interferometer (after averaging) indicates that a clear differentiation can be made between the "welded" contact bond of tantalum sputtered on steel and the approximation of the "smooth" contact bond obtained by the tantalum sheet that is epoxied to steel. The dispersion curves show that difference, as well as the differences in relative stiffness between the metallic coating and substrate.

While the invention has been particularly shown and described with respect to preferred embodiments thereof, it will be understood by those skilled in the art that changes in form and details may be made therein without departing from the scope and spirit of the invention. By example, the teaching of this invention is not limited for use only with the particular Michelson-type interferometer shown in FIG. 1. Other types of interferometers that can be used include a Fabry-Perot and Mach-Zehnder type interferometers. Also, an acoustic contact piezoelectric device can be used as long as wave parameters can be measured which can be related to the frequency content of the wave.

Thus, many modifications and variations of the present invention are possible in view of the above disclosure. Therefore to be understood that within the scope of the appended claims, the invention may be practiced otherwise than as specifically described.

What is claimed is:

1. An apparatus for determining adhesion quality of a coating on a substrate, the combined coating and substrate constituting a test specimen, the apparatus comprising:

a. the test specimen having a cylindrical surface;

b. means for generating an elastic wave within the test specimen;

c. an interferometer for detecting a responsive displacement of a surface of the test specimen;

d. means for collecting data of the elastic wave generated and determining a dispersion curve using a ridge-following technique of wavelet analysis; and;

e. means for comparing a theoretical dispersion curve of the test specimen with the observed dispersion curve as to a "welded" and "smooth" bond state of the test specimen.

2. The apparatus according to claim 1, wherein the means for generating an elastic wave comprises a laser and the interferometer includes a probe head assembly that rotates about a centerline of the probe head through a pair of optical couplers, one coupler provides an excitation beam of radiation to the test specimen and the other senses displacements generated from the test specimen, thereby enabling scanning of the cylindrical surface of the test specimen in a circular arc.

3. The apparatus according to claim 1, wherein the interferometer is selected from the group consisting of a Michelson, Fabry-Perot and Mach-Zehnder type interferometer.

4. The apparatus according to claim 1, wherein the cylindrical test specimen serves as portion of a gun bore.

5. A method for remotely detecting quality of adhesion of a bonded metal coating on a substrate, the combined coating and substrate constitutes a test specimen, comprising the steps of:

a. generating an oscillating signal that is indicative at least in part of a surface motion of the test specimen;

b. detecting an amplitude and a frequency of the generated oscillating signal; and c. generating a set of processed data that includes the detected signal and analyzing the set of processed data using a ridge-following technique using wavelet analysis, comparing the results of the ridge-following technique using associated dispersion curves of two extreme states, one state corresponding to a "welded" contact bond state and the other state corresponding to a "smooth" contact bond state that define a range of bond adhesion.

6. The method according to claim 5, wherein the test specimen serves as a gun bore.

7. An apparatus for determining adhesion quality of a coating surface on a substrate within a gun bore, the apparatus comprising:

a) impulse means for generating an impulse beam and for directing said impulse beam to the surface of the gun bore for launching an elastic wave therewithin;

b) interferometer means for detecting a displacement of the surface of the wafer in response to the launched elastic wave;

c) ridge-following technique using wavelet analysis means for determining, from said detected displacement, a time-varying characteristic of said elastic wave within the surface of the gun bore; and d) means for correlating said determined time varying characteristic with a theoretical "welded" bonding state of the surface to the substrate.

8. The apparatus according to claim 7, wherein said interferometer means includes a laser for generating an output beam, means for directing a portion of said output beam to the surface of the gun bore as a probe beam, means for generating a reference beam from a portion of said output beam, means for combining a portion of said probe beam reflecting from the surface of said gun bore surface with said reference beam, and means for detecting the displacement as a function of a change in interference between said probe beam and said reference beam.

9. The apparatus according to claim 8, wherein the interferometer means further includes a probe head assembly that rotates about a centerline of the probe head through a pair of optical couplers, a first coupler provides an excitation radiation beam from the impulse means to the test specimen through at least one lens and the other senses observed radiation from the test specimen through a detection lens, thereby enabling scanning of a cylindrical test specimen in a circular arc.

10. The apparatus according to claim 8, wherein the first coupler provides excitation radiation at two points through a pair of focusing lenses that are equidistant from the detection lens whereby the two excitation lens and the detection lens are collinear.

11. An apparatus for remotely determining adhesion quality of a coating on a substrate, a test specimen constituting the combination of a portion of the coating and the substrate being evaluated by the apparatus comprising:

a. means for generating an oscillating signal in the test specimen to produce surface motion on the test specimen;

b. means for detecting amplitude and frequency of the surface motion using a ridge following technique using wavelet analysis to provide data corresponding to the amplitude and frequency of the surface motion;

c. means for comparing data from the ridge following technique indicative of a dispersion curve of the test specimen to associated dispersion curves of two extreme states, one state corresponding to a "welded" bond state between the coating and the substrate and the other state corresponding to a "smooth" bond of the test specimen.

\* \* \* \* \*